(12) United States Patent
Minagawa et al.

(10) Patent No.: US 10,620,186 B2
(45) Date of Patent: Apr. 14, 2020

(54) METHOD FOR CAPTURING CANCER CELLS

(71) Applicants: SUMITOMO RUBBER INDUSTRIES, LTD., Kobe-shi, Hyogo (JP); YAMAGATA UNIVERSITY, Yamagata-shi, Yamagata (JP)

(72) Inventors: Yasuhisa Minagawa, Kobe (JP); Masaru Tanaka, Yonezawa (JP); Takashi Hoshiba, Yonezawa (JP); Tomokazu Shibuya, Yonezawa (JP)

(73) Assignees: SUMITOMO RUBBER INDUSTRIES, LTD., Kobe-Shi, Hyogo (JP); YAMAGATA UNIVERSITY, Yamagata (JP)

(*) Notice: Subject to any disclaimer, the term of this patent is extended or adjusted under 35 U.S.C. 154(b) by 0 days.

(21) Appl. No.: 15/692,735

(22) Filed: Aug. 31, 2017

(65) Prior Publication Data
US 2018/0088105 A1 Mar. 29, 2018

(30) Foreign Application Priority Data
Sep. 29, 2016 (JP) .................................. 2016-191618

(51) Int. Cl.
| | |
|---|---|
| *G01N 33/49* | (2006.01) |
| *C12N 5/09* | (2010.01) |
| *C08F 20/58* | (2006.01) |
| *G01N 33/50* | (2006.01) |
| *G01N 30/88* | (2006.01) |

(52) U.S. Cl.
CPC ........... *G01N 33/491* (2013.01); *C08F 20/58* (2013.01); *C12N 5/0693* (2013.01); *G01N 33/5005* (2013.01); *C12N 2533/30* (2013.01); *G01N 2030/885* (2013.01); *G01N 2030/8822* (2013.01)

(58) Field of Classification Search
CPC ............. G01N 33/491; G01N 33/5005; G01N 33/5008; C08F 20/28; C08F 20/58; C12N 2533/30
See application file for complete search history.

(56) References Cited

U.S. PATENT DOCUMENTS

| | | | |
|---|---|---|---|
| 9,372,136 B2 * | 6/2016 | Kanbara | ................ G01N 1/405 |
| 2012/0156698 A1 | 6/2012 | Jendoubi | |
| 2016/0136552 A1 | 5/2016 | Nakanishi et al. | |

FOREIGN PATENT DOCUMENTS

| | | |
|---|---|---|
| EP | 2 720 039 A1 | 4/2014 |
| JP | 2005-82538 A | 3/2005 |

(Continued)

OTHER PUBLICATIONS

Williams, PNAS 2013, 110 (13), 4861.*
(Continued)

*Primary Examiner* — Vu A Nguyen
(74) *Attorney, Agent, or Firm* — Birch, Stewart, Kolasch & Birch, LLP

(57) ABSTRACT

The present invention provides a method for capturing cancer cells which can capture many types of cancer cells, including cancer cells not expressing EpCAM. The present invention relates to a method for capturing cancer cells present in biological fluid, the method including reducing the protein level of sampled biological fluid, followed by capturing cancer cells using a hydrophilic polymer layer.

8 Claims, 1 Drawing Sheet

(56) References Cited

FOREIGN PATENT DOCUMENTS

| | | |
|---|---|---|
| JP | 2005-523981 A | 8/2005 |
| JP | 2013-174616 A | 9/2013 |
| JP | 2014-105159 A | 6/2014 |
| JP | 2015-224332 A | 12/2015 |
| JP | 2016-131561 A | 7/2016 |
| JP | 2016-168019 A | 9/2016 |
| WO | WO 03/093357 A1 | 11/2003 |
| WO | WO 2006/108087 A2 | 10/2006 |
| WO | WO 2011/017094 A2 | 2/2011 |
| WO | WO 2012/108087 A1 | 8/2012 |
| WO | WO 2015/012315 A1 | 1/2015 |
| WO | WO 2016/103002 A1 | 6/2016 |
| WO | WO 2016/115537 A2 | 7/2016 |

OTHER PUBLICATIONS

Vona et al. American Journal of Pathology, 2000, 156(1), 57-63.*
Yao et al., Integr. Biol. (Camb). Apr. 6, 2014 6(4), 388-398.*
Khoo et al., Sci. Adv. 2016, 2: e160074, 1-15.*
Hoshiba et al. RSC. Adv. 2016, 6, 89103-89112.*

* cited by examiner

A-A cross-sectional view

METHOD FOR CAPTURING CANCER CELLS

TECHNICAL FIELD

The present invention relates to a method for capturing cancer cells present in biological fluid (e.g. blood).

BACKGROUND ART

When cancer cells are formed, they are known to appear in due course in blood or biological fluid. Such cancer cells in blood are called "circulating tumor cells (CTCs)". Thus, it can be expected that the circulating tumor cells are examined, e.g., to confirm the cancer-treating effect, predict prognosis life expectancy, predict the effect of anticancer drugs before administration, or examine treatment methods through genetic analysis of cancer cells.

However, a problem exists in that since the number of circulating tumor cells is very small (several to hundreds of cells/1 mL of blood), such cancer cells are difficult to capture.

For example, the CellSearch System is known as a technique for capturing circulating tumor cells. This technique, which utilizes an antigen-antibody reaction (capture by EpCAM antibody), can only capture cancer cells expressing EpCAM, and the types of capturable cancer cells are limited.

CITATION LIST

Patent Literature

Patent Literature 1: JP 2005-523981 T

SUMMARY OF INVENTION

Technical Problem

The present invention aims to solve the above problem and provide a method for capturing cancer cells which can capture many types of cancer cells, including cancer cells not expressing EpCAM.

Solution to Problem

The present invention relates to a method for capturing cancer cells present in biological fluid, the method including reducing a protein level of sampled biological fluid, followed by capturing cancer cells using a hydrophilic polymer layer.

The hydrophilic polymer layer is preferably formed of at least one hydrophilic polymer selected from the group consisting of poly(meth)acryloylmorpholine and a polymer represented by the formula (I):

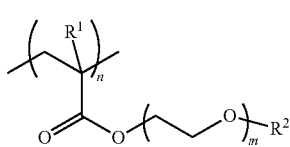

wherein $R^1$ represents a hydrogen atom or a methyl group, $R^2$ represents an alkyl group, m represents 1 to 5, and n represents the number of repetitions.

The hydrophilic polymer layer is preferably formed of a copolymer of at least one hydrophilic monomer selected from the group consisting of (meth)acryloylmorpholine and a compound represented by the formula (I-1):

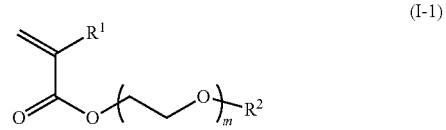

wherein $R^1$, $R^2$, and m are as defined above, with a second monomer.

The protein level is preferably reduced by diluting the sampled biological fluid. The dilution is preferably carried out with a buffer solution or a liquid medium.

The protein level is preferably reduced by centrifuging the sampled biological fluid and removing a supernatant.

The biological fluid is preferably blood.

The hydrophilic polymer layer preferably has a thickness of 2 to 200 nm.

Advantageous Effects of Invention

The method for capturing cancer cells present in biological fluid according to the present invention includes reducing the protein level of sampled biological fluid, followed by capturing cancer cells using a hydrophilic polymer layer. Such a method can capture many types of cancer cells, including cancer cells not expressing EpCAM. Thus, for example, it is possible to sufficiently capture cancer cells from biological fluid while reducing the adhesion or attachment of other proteins and cells, thereby selectively capturing the cancer cells.

DESCRIPTION OF EMBODIMENTS

The present invention relates to a method for capturing cancer cells present in biological fluid. The method includes reducing the protein level of sampled biological fluid, followed by capturing cancer cells using a hydrophilic polymer layer.

In this method, sampled biological fluid is first subjected to a treatment such as dilution or centrifugation to prepare a sample having a lower protein level than the sampled biological fluid, and the sample is brought into contact with a hydrophilic polymer layer to capture cancer cells in the sample. Accordingly, since proteins such as albumin have a reduced effect in inhibition of cell adhesion, and intrinsic adhesion of cancer cells to the hydrophilic polymer is provided, the ability to capture cancer cells is greatly improved while reducing the ability to capture platelets and others. As a result, an effect which could never be produced when proteins are present at high levels is achieved in selectively capturing cancer cells.

Specifically, since the number of tumor cells (e.g. cancer cells) appearing in biological fluid, such as circulating tumor cells (several to hundreds of cells/1 mL of blood), is very small, it is important to capture as many tumor cells present in the sampled biological fluid as possible to analyze them. It is thus considered that it is necessary to reduce the number of proteins that inhibit adhesion of tumor cells. In the method of the present invention, a sample having a lower protein level than the sampled biological fluid is previously prepared, and then brought into contact with a hydrophilic polymer layer. Accordingly, more tumor cells in the biological fluid adsorb or adhere to the hydrophilic polymer layer. Then, it can be expected that the number of adsorbed tumor cells is counted to determine the number of tumor cells in the biological fluid, e.g., in order to confirm the cancer-treating effect. Moreover, the captured tumor cells may be cultured and then used to determine the effect of drugs such as anticancer drugs. This allows us to determine the effect of drugs such as anticancer drugs ex vivo before administration, and also helps to screen drugs such as anticancer drugs.

Examples of preferred embodiments of the present invention are described below with reference to drawings.

Figure 1A:
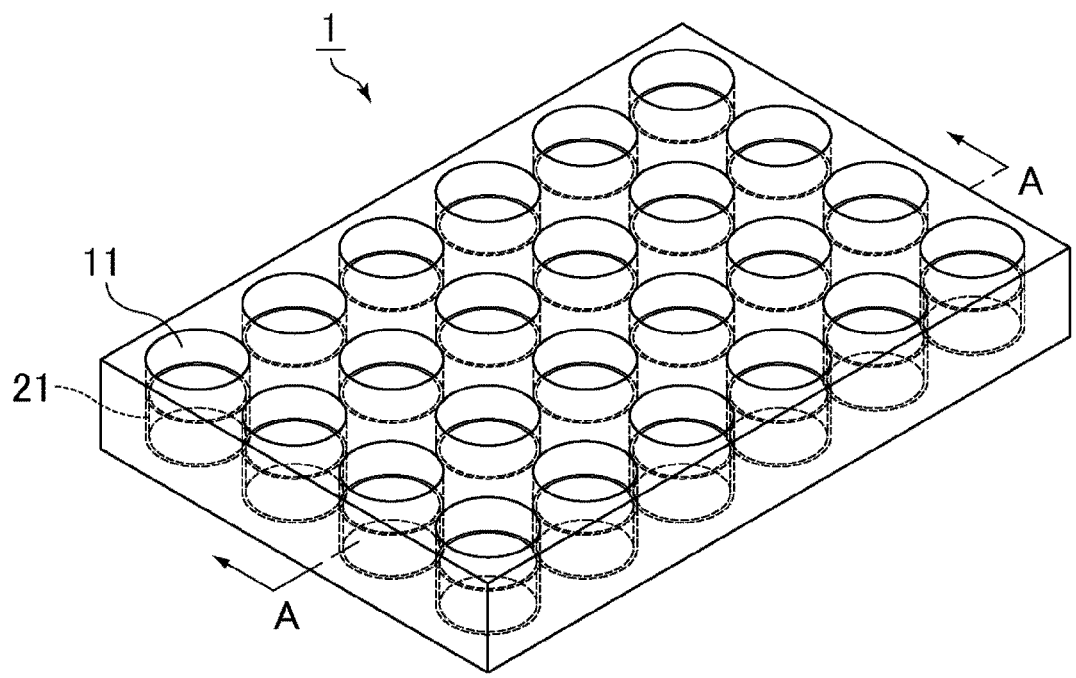
FIGS. 1A and 1B are exemplary schematic views of a multi-well plate (medical analysis device) having wells with a hydrophilic polymer layer formed thereon.
Figure 1B:
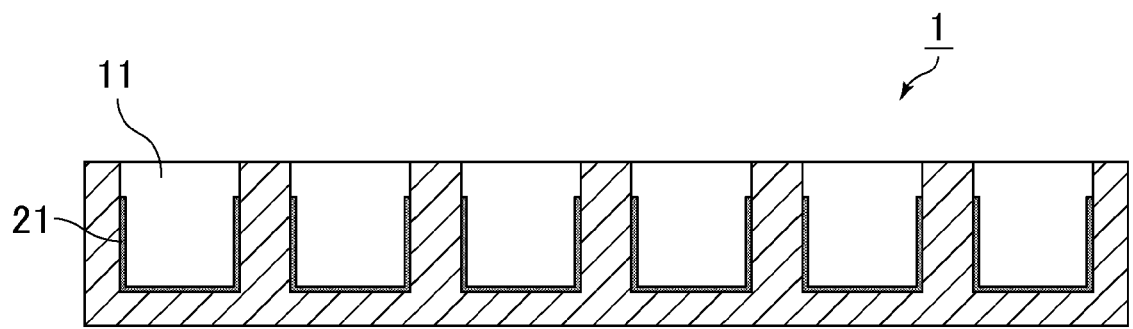

The method for capturing cancer cells of the present invention can be carried out using, for example, a medical analysis device 1 (multi-well plate 1) illustrated in FIGS. 1A and 1B.

A medical analysis device 1 (multi-well plate 1) illustrated in FIGS. 1A and 1B is a device intended to capture cancer cells in which wells 11 are arranged in so-called matrix form. The multi-well plate 1 has multiple wells 11 having a circular opening. The wells 11 are recesses into which a sample prepared by reducing the protein level of biological fluid such as blood is injected. Cancer cells can be efficiently captured when the injected sample is subjected to analysis as compared to when the sampled biological fluid is directly subjected to analysis. Consequently, it is possible to confirm the presence or absence of cancer cells in the biological fluid, count the number of cancer cells, culture the cancer cells, determine the effect of drugs, and screen the drugs.

The protein level of biological fluid can be reduced by known methods, such as by diluting the sampled biological fluid. The dilution may be carried out with a buffer solution such as a phosphate buffered saline (PBS) having the same pH as human blood (about 7.4) or a liquid medium such as Dulbecco's modified eagle's medium (DMEM). Specifically, a sample having a lower protein level than the sampled biological fluid can be prepared by diluting the sampled biological fluid by adding a buffer solution to the sampled biological fluid or adding the sampled biological fluid to a liquid medium.

The protein level of biological fluid may also be reduced by centrifuging the sampled biological fluid and removing the supernatant. Specifically, the sampled biological fluid is centrifuged, followed by removing the resulting supernatant containing proteins to prepare a sample having a lower protein level than the sampled biological fluid.

Although FIGS. 1A and 1B show a 24-well plate having 24 wells 11 arranged in 4 rows by 6 columns as an example, it is sufficient for the multi-well plate 1 to have at least two wells 11, and any number of wells 11 may be provided. Examples other than the 24-well plate include general multi-well plates in which the number of wells 11 is 6, 96, 384, etc.

Examples of the material of the multi-well plate 1 include acrylic resins (polyacrylic resins) such as polymethyl acrylate, polymethyl methacrylate, polyacrylic acid, and polymethacrylic acid, cycloolefin resins (polycycloolefins), carbonate resins (polycarbonates), styrene resins (polystyrenes), polyester resins such as polyethylene terephthalate (PET), and polydimethylsiloxanes.

Each well 11 is a non-through hole which is opened at the surface of the multi-well plate 1. A sample prepared by reducing the protein level of biological fluid is injected into the wells 11 through the respective openings. If the presence of cancer cells is confirmed, a culture fluid for culturing the cancer cells may also be injected.

The diameter R and depth D of the opening of each well 11 are not particularly limited, and may be those of a conventional multi-well plate 1. Although in FIGS. 1A and 1B, the inner side surface of each well 11 is substantially vertical to the opposite sides of the multi-well plate 1, the inner side surface of each well 11 may be inclined to taper from the opening to the bottom. Alternatively, the inner side surface may be inclined to flare out from the opening to the bottom.

Though the wells 11 in FIGS. 1A and 1B are circularly opened, the opening of the wells 11 may be of any shape such as a quadrangle.

The multi-well plate 1 may suitably be one in which the multiple wells 11 are separable. Since multiple wells are provided, they can be separated into wells for counting the number of cancer cells and for culturing cancer cells. For example, the presence or absence of cancer cells is first confirmed in the wells for counting, and if the presence is confirmed, the cancer cells are cultured in the wells for culturing and then used to determine the effect of drugs.

In the multi-well plate 1 (medical analysis device 1), each well 11 preferably has a hydrophilic polymer layer formed at least partly on the inner surface thereof. FIGS. 1A and 1B illustrate a case where a hydrophilic polymer layer 21 is formed on the bottom surface and a part of the side surface of the wells.

Once a sample prepared by reducing the protein level of biological fluid is introduced into the wells 11, cancer cells present in the sample adsorb onto the hydrophilic polymer layer 21, while the adsorption of other cells such as platelets and erythrocytes is reduced. Thus, cancer cells can be adsorbed onto the hydrophilic polymer layer 21 by introducing and retaining the sample in the wells for a predetermined time, followed by washing. Then, it can be expected that the number of adsorbed cancer cells is counted to determine the number of cancer cells in the biological fluid, e.g., in order to confirm the cancer-treating effect.

The thickness (film thickness) of the hydrophilic polymer layer 21 (layer formed of a hydrophilic polymer) is preferably 2 to 200 nm, more preferably 20 to 180 nm. When the thickness is adjusted within the range indicated above, selective adsorption or adhesion of cancer cells, and low adsorption of other proteins and cells can be well achieved.

The hydrophilic polymer may be appropriately selected from polymers having hydrophilicity. For example, it may be a homopolymer or copolymer of one or two or more hydrophilic monomers, or a copolymer of one or two or more hydrophilic monomers with a second monomer. Examples of the homopolymer and copolymers include polyacrylic acid, polyacrylic acid esters, polymethacrylic acid, polymethacrylic acid esters, polyacryloylmorpholine, polymethacryloylmorpholine, polyacrylamide, and polymethacrylamide.

The hydrophilic monomer may be any monomer containing a hydrophilic group. Examples of the hydrophilic group include known hydrophilic groups such as an amide group, a sulfuric acid group, a sulfonic acid group, a carboxylic acid group, a hydroxy group, an amino group, and an oxyethylene group.

Specific examples of the hydrophilic monomer include (meth)acrylic acid, (meth)acrylic acid esters (e.g. alkoxyalkyl (meth)acrylates such as methoxyethyl (meth)acrylate, and hydroxyalkyl (meth)acrylates such as hydroxyethyl (meth)acrylate), (meth)acrylamide, and (meth)acrylamide derivatives containing cyclic groups (e.g. (meth)acryloylmorpholine).

The second monomer may be appropriately selected as long as it does not inhibit the effect of the hydrophilic polymer. Examples include aromatic monomers such as styrene, vinyl acetate, and N-isopropylacrylamide which can impart temperature responsiveness.

In particular, the hydrophilic polymer is preferably at least one selected from the group consisting of poly(meth)acryloylmorpholine and a polymer represented by the following formula (I):

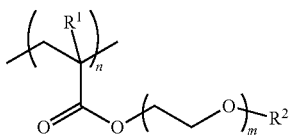
(I)

wherein $R^1$ represents a hydrogen atom or a methyl group, $R^2$ represents an alkyl group, m represents 1 to 5, and n represents the number of repetitions.

The alkyl group represented by $R^2$ preferably has a carbon number of 1 to 10, more preferably 1 to 5. In particular, $R^2$ is particularly preferably a methyl group or an ethyl group. The symbol m is preferably 1 to 3, while n (number of repeating units) is preferably 15 to 1,000, more preferably 30 to 500.

Alternatively, the hydrophilic polymer may also suitably be a copolymer of at least one hydrophilic monomer selected from the group consisting of (meth)acryloylmorpholine and a compound represented by the following formula (I-1):

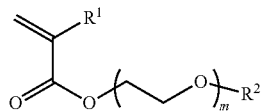
(I-1)

wherein $R^1$, $R^2$, and m are as defined above, with a second monomer.

From the standpoint of selective adsorption or adhesion to cancer cells, the hydrophilic polymer preferably has a weight average molecular weight (Mw) of 4,000 to 150,000, more preferably 5,000 to 100,000, still more preferably 8,000 to 50,000. The Mw as used herein can be determined by gel permeation chromatography (GPC) (GPC-8000 series produced by TOSOH Corporation, detector: differential refractometer, column: TSKGEL SUPERMULTIPORE HZ-M produced by TOSOH Corporation) calibrated with polystyrene standards.

The medical analysis device can be produced, for example, by preparing a multi-well plate 1 including wells 11 as illustrated in FIGS. 1A and 1B, optionally followed by addition of other members (parts).

Specifically, when it is desired to produce a multi-well plate 1 with a hydrophilic polymer layer 21 formed thereon, the multi-well plate 1 provided with a polymer layer formed of a hydrophilic polymer can be produced by dissolving or dispersing a hydrophilic polymer in any solvent to prepare a hydrophilic polymer solution or dispersion, and entirely or partially coating the inner surface of each well 11 with the hydrophilic polymer solution or dispersion by a known method, such as (1) by injecting the hydrophilic polymer solution or dispersion into the wells 11 and retaining it for a predetermined time, or (2) by applying (spraying) the hydrophilic polymer solution or dispersion to the inner surface of the wells 11. Then, other parts, if necessary, are added to the prepared multi-well plate 1, whereby a medical analysis device can be produced.

The solvent, injection method, application (spraying) method, and other conditions may be conventionally known materials or methods.

The retention time in the method (1) or (2) may be selected appropriately according to the size of the wells 11, the type of liquid introduced, and other factors, and is preferably five minutes to ten hours, more preferably ten minutes to five hours, still more preferably 15 minutes to two hours. After the retention, the excess hydrophilic polymer solution or dispersion may be discharged followed by drying, as required.

EXAMPLES

The present invention is specifically described with reference to examples below, but is not limited thereto.
(Production of Medical Analysis Device (Multi-Well Plate))

2-methoxyethyl acrylate was thermally polymerized at 80° C. for six hours using azobisisobutyronitrile (AIBN) to produce poly(2-methoxyethyl acrylate) (molecular weight Mn=about 15,000, Mw=about 50,000). Then, a 2.5 w/v % solution of the poly(2-methoxyethyl acrylate) in methanol was prepared.

The poly(2-methoxyethyl acrylate) solution (2.5 w/v %) was injected into a commercially available PMMA plate, and left for 30 minutes at room temperature. Thereafter, the solution was drawn using a pipette, followed by drying to prepare an analysis device including a multi-well plate with a hydrophilic polymer layer formed thereon as illustrated in FIGS. 1A and 1B.

Example 1

Fibrosarcoma (HT-1080) was suspended in a PBS solution (phosphate buffered saline), and the number of cells was counted using a blood cell counter. Then, a PBS solution was further added to adjust the cell concentration in the PBS solution to a predetermined value (A1). Next, the mixture was resuspended in blood so that the calculated plating density (concentration) was 2,850 cells/cm$^2$. In this example, blood and an equal amount of a PBS solution were added.

Example 2

Fibrosarcoma (HT-1080) was suspended in a PBS solution (phosphate buffered saline), and the number of cells was counted using a blood cell counter. Then, a PBS solution was further added to adjust the cell concentration in the PBS solution to a predetermined value (A2). Next, the mixture was resuspended in blood so that the calculated plating density (concentration) was 2,850 cells/cm$^2$. In this example, blood and a double amount of a PBS solution were added.

Example 3

Fibrosarcoma (HT-1080) was suspended in DMEM (liquid medium), and the number of cells was counted using a blood cell counter. Then, DMEM was further added to adjust the cell concentration in the DMEM to a predetermined value (A1). Next, the mixture was resuspended in blood so that the calculated plating density (concentration) was 2,850 cells/cm$^2$. In this example, blood and an equal amount of DMEM were added.

Example 4

Fibrosarcoma (HT-1080) was suspended in DMEM (liquid medium), and the number of cells was counted using a blood cell counter. Then, DMEM was further added to adjust the cell concentration in the DMEM to a predetermined value (A2). Next, the mixture was resuspended in blood so that the calculated plating density (concentration) was 2,850 cells/cm$^2$. In this example, blood and a double amount of DMEM were added.

Example 5

Fibrosarcoma (HT-1080) was suspended in a dissociation solution and a portion of the suspension was resuspended in a PBS solution to count the number of cells using a blood cell counter. Using the obtained number, the dissociation solution containing fibrosarcoma (HT-1080) was resuspended in blood so that the calculated plating density (concentration) was 2,850 cells/cm$^2$. Next, the resuspended blood was centrifuged (3,000 rpm, 10 minutes), the supernatant was discharged, and the remaining blood was taken out.

Example 6

Fibrosarcoma (HT-1080) was suspended in a dissociation solution and a portion of the suspension was resuspended in a PBS solution to count the number of cells using a blood cell counter. Using the obtained number, the dissociation solution containing fibrosarcoma (HT-1080) was resuspended in blood so that the calculated plating density (concentration) was 2,850 cells/cm$^2$. Next, the resuspended blood was centrifuged (3,000 rpm, 5 minutes), the supernatant was discharged, and the remaining blood was taken out.

Example 7

Fibrosarcoma (HT-1080) was suspended in a dissociation solution and a portion of the suspension was resuspended in a PBS solution to count the number of cells using a blood cell counter. Using the obtained number, the dissociation solution containing fibrosarcoma (HT-1080) was resuspended in blood so that the calculated plating density (concentration) was 2,850 cells/cm$^2$. Next, the resuspended blood was centrifuged (1,500 rpm, 10 minutes), the supernatant was discharged, and the remaining blood was taken out.

Comparative Example 1

Fibrosarcoma (HT-1080) was suspended in a dissociation solution and a portion of the suspension was resuspended in a PBS solution to count the number of cells using a blood cell counter. Using the obtained number, the dissociation solution containing fibrosarcoma (HT-1080) was resuspended in blood so that the calculated plating density (concentration) was 2,850 cells/cm$^2$.

The test samples (samples having a lower protein level than the sampled blood) prepared in the examples and comparative example were evaluated using the medical analysis device illustrated in FIGS. 1A and 1B, as follows.

(Thickness of Hydrophilic Polymer Layer (Coating Layer))

The thickness of the hydrophilic polymer layer on the inner surface of the wells was measured (photographed) using a TEM at an accelerating voltage of 15 kV and a magnification of 1,000 times.

(Counting of Number of Cancer Cells)

A 1 ml portion of each test sample (cancer cell-containing blood) was injected into each well and left at 37° C. for one hour to cause adhesion. Then, non-adhering cells were washed away with a PBS solution. Subsequently, immunostaining was performed, and the number of adhering cancer cells was counted using a fluorescence microscope. The numbers of adhering cells are compared relative to Comparative Example 1 set equal to 1.0.

TABLE 1

|  | Example | | | | | | | Comparative Example |
| --- | --- | --- | --- | --- | --- | --- | --- | --- |
|  | 1 | 2 | 3 | 4 | 5 | 6 | 7 | 1 |
| Thickness of hydrophilic polymer layer (nm) | 88 | 88 | 88 | 88 | 88 | 88 | 88 | 88 |
| Amount of adhering cancer cells | 3.5 | 3.2 | 3.7 | 3.5 | 4.1 | 3.9 | 3.8 | 1.0 |

It is demonstrated that the amount of adhering cancer cells was greatly increased in the examples in which analysis was performed on a sample prepared by reducing the protein level by diluting the sampled blood with a PBS solution or a liquid medium or by centrifuging the blood and removing the supernatant, when compared to Comparative Example 1 in which the sampled blood was directly subjected to analysis.

REFERENCE SIGNS LIST

1: Medical analysis device (multi-well plate)
11: Well
21: Hydrophilic polymer layer

The invention claimed is:
1. A method for capturing cancer cells present in biological fluid, the method comprising:
reducing an albumin level of sampled biological fluid, followed by capturing cancer cells using a hydrophilic polymer layer,
wherein the hydrophilic polymer layer is formed at least partly on an inner surface of a well of a non-through hole,
wherein the hydrophilic polymer layer has a thickness of 20 to 200 nm, and wherein the hydrophilic polymer layer is formed of at least one hydrophilic polymer selected from the group consisting of:
(i) poly(meth)acryloylmorpholine,
(ii) a polymer represented by the formula (I):

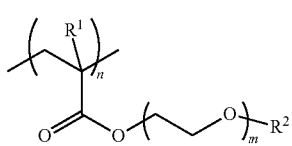

(I)

wherein $R^1$ represents a hydrogen atom or a methyl group, $R^2$ represents an alkyl group, m represents 1 to 5, and n represents the number of repetitions, and
(iii) a copolymer of at least one hydrophilic monomer selected from the group consisting of (meth)acryloylmorpholine and a compound represented by the formula (I-1):

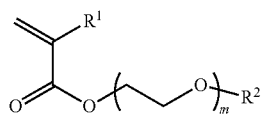

(I-1)

wherein $R^1$ represents a hydrogen atom or a methyl group, $R^2$ represents an alkyl group, and m represents 1 to 5, with a second monomer.

2. The method for capturing cancer cells according to claim 1,
wherein the albumin level is reduced by diluting the sampled biological fluid.

3. The method for capturing cancer cells according to claim 2,
wherein the dilution is carried out with a buffer solution or a liquid medium.

4. The method for capturing cancer cells according to claim 1,
wherein the albumin level is reduced by centrifuging the sampled biological fluid and removing a supernatant.

5. The method for capturing cancer cells according to claim 1,
wherein the biological fluid is blood.

6. The method for capturing cancer cells according to claim 1,
wherein the well of a non-through hole is a multi-well.

7. A method for confirming an effect of drugs, the method comprising
capturing cancer cells by the method for capturing cancer cells according to claim 1, and
confirming the effect of drugs against cancer cells using the captured cancer cells.

8. The method for capturing cancer cells according to claim 1, wherein the hydrophilic polymer layer has a thickness of 20 to 180 nm.

* * * * *